United States Patent
Martin et al.

(12)

(10) Patent No.: US 6,372,723 B1
(45) Date of Patent: Apr. 16, 2002

(54) COMPOSITIONS AND METHODS FOR PREVENTING RESTENOSIS FOLLOWING REVASCULARIZATION PROCEDURES

(75) Inventors: Pauline L. Martin, Boston, MA (US); Donald A. McAfee, Richmond, VA (US)

(73) Assignee: Discovery Therapeutics, Inc., Richmond, VA (US)

( * ) Notice: Subject to any disclaimer, the term of this patent is extended or adjusted under 35 U.S.C. 154(b) by 0 days.

(21) Appl. No.: 09/456,432

(22) Filed: Dec. 8, 1999

Related U.S. Application Data

(63) Continuation of application No. PCT/US98/12717, filed on Jun. 18, 1998.
(60) Provisional application No. 60/050,031, filed on Jun. 18, 1997.

(51) Int. Cl.$^7$ ............................................... A61K 31/70
(52) U.S. Cl. .......................................... 514/45; 514/46
(58) Field of Search ..................... 514/45, 46

(56) References Cited

U.S. PATENT DOCUMENTS

| | | | |
|---|---|---|---|
| 4,783,530 A | 11/1988 | Rzeszotarski et al. | 544/267 |
| 4,977,144 A | 12/1990 | Fujimoto et al. | 514/46 |
| 5,034,381 A | 7/1991 | Hutchinson et al. | 514/26 |
| 5,140,015 A | 8/1992 | Olsson et al. | 514/46 |
| 5,189,027 A | 2/1993 | Miyashita et al. | 514/46 |
| 5,208,240 A | 5/1993 | Peet et al. | 514/263 |
| 5,278,150 A | 1/1994 | Olsson et al. | 514/46 |
| 5,290,782 A | 3/1994 | Suzuki et al. | 514/263 |
| 5,342,841 A | 8/1994 | Suzuki et al. | 514/263 |
| 5,395,836 A | 3/1995 | Shimada et al. | 514/263 |
| 5,443,836 A | 8/1995 | Downey et al. | 424/423 |
| 5,446,046 A | 8/1995 | Belardinelli et al. | 514/263 |
| 5,449,665 A | * 9/1995 | Sollevi | 514/46 |
| 5,453,426 A | 9/1995 | Jacobsen et al. | 514/263 |
| 5,459,132 A | * 10/1995 | Bru-Magniez et al. | 514/46 |
| 5,525,607 A | 6/1996 | Suzuki et al. | 514/263 |
| 5,534,504 A | 7/1996 | Sollevi et al. | 514/46 |
| 5,733,925 A | 3/1998 | Kunz et al. | 514/449 |
| 5,773,423 A | 6/1998 | Jacobson et al. | 514/45 |
| 5,877,180 A | * 3/1999 | Linden et al. | 514/266 |
| 5,932,558 A | * 8/1999 | Cronstein et al. | 514/46 |

FOREIGN PATENT DOCUMENTS

| | | |
|---|---|---|
| GB | 2 289 218 A | 11/1995 |
| WO | WO 99/17784 | 4/1999 |
| WO | WO 99/34804 | 7/1999 |

OTHER PUBLICATIONS

Baj, Z., et al., "The effect of short–term myocardial ischemic on the expression of adhesion molecules and the oxidative burst of coronary sinus blood neutrophils," *Atherosclerosis* 106:159–168 (1994).

Barry, W.L. and Sarembock, I.J., "Antiplatelet and Anticoagulant Therapy in Patients Undergoing Percutaneous Transluminal Coronary Angioplasty," *Cardiology Clinics* 12:517–535 (1994).

Belardinelli, L., et al., "1,3–Dipropyl–8–[2–(5,6–Epoxy)Norbornyl]Xanthine, a Potent, Specific and Selective $A_1$ Adenosine Receptor Antagonist in the Guinea Pig Heart and Brain and in $DDT_1MF$–2 Cells," *J. Pharmacol. Exp. Ther.* 275:1167–1176 (1995).

Bullough, D.A., et al., "Adenosine Activates $A_2$ Receptors to Inhibit Neutrophil Adhesion and Injury to Isolated Cardiac Myocytes," *J. Immunol.* 155:2579–2586 (1995).

Cristalli, G., et al., "Inhibition of platelet aggregation by adenosine receptor agonists," *Arch Pharmacol.* 349:644–650 (1994).

Cronstein, B.N., et al., "Adenosine; A Physiologic Modulator of Superoxide Anion Generation by Human Neutrophils. Adenosine Acts Via an $A_2$ Receptor on Human Neutrophils," *J. Immunol.* 135:1366–1371 (1985).

Cronstein, B.N., et al., "The Adenosine/Neutrophil Paradox Resolved: Human Neutrophils Possess Both $A_1$ and $A_2$ Receptors that Promote Chemotaxis and Inhibit $O_2$ Generation, Respectively," *J. Clin. Invest.* 85:1150–1157 (1990).

Cronstein, B.N., et al., "Neutrophil Adherence to Endothelium is Enhanced Via Adenosine $A_1$ Receptors and Inhibited Via Adenosine $A_2$ Receptors," *J. Immunol.* 148:2201–2206 (1992).

Cronstein, B.N., et al., Methotrexate Inhibits Leukocyte Influx into Inflammatory Sites Via the Adenosine ($A_2$) Receptor, *Clin. Res.* 41:224A (1993).

Cronstein, B.N., "A Novel Approach to the Development of Anti–inflammatory Agents: Adenosine Release at Inflamed Sites," *J. Invest. Med.* 43:50–57 (1995).

de la Harpe, J. and Nathan, C.F., "Adenosine Regulates the Respiratory Burst of Cytokine–Triggered Human Neutrophils Adherent to Biologic Surfaces," *J. Immunol.* 143:596–602 (1989).

Gasperetti, C.M., et al., "Platelet Activation During Coronary Angioplasty in Humans," *Circulation* 88:2728–2734 (1993).

(List continued on next page.)

*Primary Examiner*—James O. Wilson
(74) *Attorney, Agent, or Firm*—Sterne, Kessler, Goldstein & Fox PLLC

(57) ABSTRACT

In the present invention, a method is provided which reduces or prevents restenosis following revascularization procedures. It has now been found that selective stimulation of adenosine $A_{2A}$ receptors can reduce or prevent such restenosis. This method may be achieved either by: (a) the administration of selective adenosine $A_{2A}$ receptor agonists, (b) the administration of a selective adenosine $A_1$ antagonist in combination with either a selective adenosine $A_{2A}$ receptor agonist or a non-selective adenosine agonist, or (c) the administration of a selective adenosine $A_1$ antagonist in order to block adenosine $A_1$ receptor activation by endogenously-released adenosine. The present invention is also directed to an improved surgical procedure that relies upon selective stimulation of adenosine $A_{2A}$ receptors.

16 Claims, No Drawings

OTHER PUBLICATIONS

Glover, D.K., et al., "Pharmacological Stress Thallium Scintigraphy With 2–Cyclohexylmethylidenehydrazinoadenosine (WRC–0470): A Novel, Short–Acting Adenosine $A_{2A}$ Receptor Agonist," *Circulation* 94:1726–1732 (Oct. 1996).

Ikeda, H., et al., "Neutrophil activation after percutaneous transluminal coronary angioplasty," *Am. Heart J.* 128:1091–1098 (1994).

Männel, D.N., et al., "Tumor Necrosis Factor: A Cytokine Involved in Toxic Effects of Endotoxin," *Rev. Infect. Dis.* 9:s602–S606 (1987).

Merhi, Y., et al., "Neutrophil Implications in Platelet Deposition and Vasoconstriction After Deep Arterial Injury by Angioplasty in Pigs," *Circulation* 90:997–1002 (1994).

Mickelson, J.K., et al., "Leukocyte Activation With Platelet Adhesion After Coronary Angioplasty: A Mechanism for Recurrent Disease?," *J. Am. Coll. Cardiol.* 28:345–353 (Aug. 1996).

Neumann, F.–J., et al., "Cardiac Release of Cytokines and Inflammatory Responses in Acute Myocardial Infarction," *Circulation* 92:748–755 (1995).

Neumann, F.–J., et al., "Ischaemia induced by coronary balloon angioplasty. Cardiac release of chemoattractants," *Br. Heart J.* 70:27–54 (1993).

Neumann, F.–J., et al., "Neutrophil and Platelet Activation in Balloon–Injured Coronary Artery Plaque in Patients Undergoing Angioplasty," *J. Am. Coll. Cardiol.* 27:819–824 (Mar. 1996).

Niiya, K., et al., "2–(N'–Aralkylidenehydrazino)adenosines: Potent and Selective Coronary Vasodilators," *J. Mol. Chem.* 35:4562–4566 (1992).

Niiya, K., et al., "2–(N'–Alkylidenehydrazino)adenosines: Potent and Selective Coronary Vasodilators," *J. Mol. Chem.* 35:4557–4561 (1992).

Pärsson, H., et al., "Deposition of Platelets and Neutrophils in Porcine Iliac Arteries after Angioplasty and Wallstent Placement Compared with Angioplasty Alone," *Cardiovasc. Intervent. Radiol.* 17:190–196 (1994).

Provost, P. & Merhi, Y., "BW755C, a Dual Lipoxygenase/Cyclooxygenase Inhibitor, Reduces Mural Platelet and Neutrophil Deposition and Vasoconstriction After Angioplasty Injury in Pigs,"*J. Pharmacol. Environ. Ther.* 277:17–21 (Apr. 1996).

Ragosta, M., et al., "Effect of Thrombin Inhibition With Desulfatohirudin on Early Kinetics of Cellular Proliferation After Balloon Angioplasty in Atherosclerotic Rabbits," *Circulation* 93:1194–1200 (Mar. 1996).

Seekamp, A and Ward, P.A., "Ischemia—Reperfusion Injury," in *Inflam. Disease Therapy: Preclinical and Clinical Developments*, Bonney, J.R., et al., eds., Berkhäaser Verlag, Basel , pp. 137–152 (1993).

Siminiak, T., et al., "Plasma mediated neutrophil stimulation during coronary angioplasty: autocrine effect of platelet activating factor," *Br. Heart J.* 74:625–630 (1995).

Sullivan, G.W., et al., "The Specific Type IV Phosphodiesterase Inhibitor Rolipram Combined with Andeosine Reduces Tumor Necrosis Factor–α–Primed Neutrophil Oxidative Activity," *Int. J. Immunopharmac.* 17:793–803 (1995).

Tracey, K.J., et al., "Cachectin/Tumor Necrosis Factor Induces Cachexia, Anemia, and Inflammation," *J. Exp. Med.* 167:1211–1227 (1988).

Ueeda, M., et al., "2–Alkoxyadenosines: Potent and Selective Agonists at the Coronary Artery $A_2$ Adenosine Receptor," *J. Med. Chem.* 34:1334–1339 (1991).

Ueeda, M., et al., "2–Aralkoxyadenosines: Potent and Selective Agonists at the Coronary Artery $A_2$ Adenosine Receptor," *J. Med. Chem.* 34:1340–1344 (1991).

Varani, K., et al., "Binding characteristics of the adenosine $A_2$ receptor ligand [$H^3$]HCGS 21680 to human platelet membranes," *Biochem. Pharmacol.* 48:1658–1661 (1994).

* cited by examiner

COMPOSITIONS AND METHODS FOR PREVENTING RESTENOSIS FOLLOWING REVASCULARIZATION PROCEDURES

This application is a continuation of International Patent Application No. PCT/US98/12717, filed Jun. 18, 1998, which claims priority to U.S. Provisional Patent Application No. 60/050,031, filed Jun. 18, 1997. The contents of both applications are entirely incorporated by reference herein.

BACKGROUND OF THE INVENTION

1. Field of the Invention

The present invention relates to adenosine pharmacology and improved surgical procedures. More particularly, the invention relates to reducing or preventing restenosis following a revascularization procedure by selective activation of adenosine $A_{2A}$ receptors.

2. Related Art

Occlusion of blood vessels can be treated with revascularization procedures that attempt to either remove the occlusion or to reroute blood flow through a bypass graft. A variety of surgical approaches have been used, including percutaneous transluminal coronary angioplasty (PTCA), directional coronary atherectomy (DCA) and excimer laser angioplasty. In order to provide improved blood flow in the heart, for example, the insertion of coronary artery bypass grafts has become common practice. PTCA is an alternative procedure that is also conducted in patients whose coronary blood flow is severely impaired by the presence of atherosclerotic plaques within the coronary blood vessels. In this procedure, a balloon catheter is inserted into coronary blood vessels and inflated at the site of the stenosis in an attempt to disrupt the atherosclerotic plaque and/or distend the disease-free area of the vessel to restore coronary blood flow. This procedure is conducted in approximately 300,000 patients a year in the United States. Although the procedure is highly successful at relieving the stenosis and restoring coronary blood flow, the utility of the procedure is hampered by abrupt closure of the vessels in about 5% of patients (no re-flow phenomenon), and by restenosis in 30% to 40% of patients within three to six months of the procedure (Barry, W. L. and Sarembock, I. J., *Anticoag Antiplatelet Ther.* 12:517–535 (1994)). Restenosis can be described as an exaggerated form of vascular repair following arterial injury. New devices and a variety of pharmacological strategies have not been successful at eliminating this problem.

Numerous studies have been conducted in an attempt to elucidate the mechanism of restenosis following angioplasty. A large body of evidence is available that suggests that a neutrophil/platelet interaction is involved. The angioplasty procedure produces brief periods of myocardial ischemia. Current evidence suggests that activation of neutrophils during ischemia results in injury by: (a) the release of oxygen free radicals, proteolytic enzymes, and leukotoxin, (b) aggregation and adherence of neutrophils to endothelial cells and subsequent capillary plugging and impairment of coronary blood flow, and (c) vasoconstriction that may result from leukotriene $B_4$ release by activated neutrophils. Platelets are activated by the release of oxygen free radicals, leukotrienes and platelet activating factor from activated neutrophils. Deposition of platelets and thrombus formation have been shown to contribute to restenosis following angioplasty. The activated platelets release vasoconstrictor substances including thromboxane, serotonin and adenine nucleotides. In addition, platelets release platelet-derived growth factor which causes proliferation of vascular smooth muscle cells.

A primary stimulus for restenosis appears to be the activation of neutrophils in response to ischemia during the angioplasty procedure. Numerous clinical studies have shown an increased expression of surface adhesion molecules on neutrophils in blood taken from the coronary sinus following angioplasty (Mickelson, J. K., et al., *JACC* 28:345–353 (1996); Ikeda, H., et al., *Am. Heart J.* 128:1091–1098 (1994); Neumann et al., *Circulation* 92:748–755 (1995); Neumann et al., *J. Am. Coll. Cardiol.* 27:819–824 (1996); Siminiak, T., et al., *Br. Heart J.* 74:625–630 (1995); and Baj, Z., et al., *Atherosclerosis* 106:159–168 (1994)). In addition, neutrophils taken from the coronary sinus following angioplasty show an increased release of toxic oxygen products and elastase when tested ex vivo (Ikeda, H., et al., *Am. Heart J.* 128:1091–1098 (1994)) and plasma from the coronary sinus causes an activation of normal neutrophils ex vivo (Neumann, F-J., et al., *Br. Heart J.* 70:27–34 (1993)).

Adenosine is an endogenous signal molecule that is released into the circulation during periods of ischemia. Adenosine exerts its physiological actions by activation of four subtypes of adenosine receptors designated $A_1$, $A_{2A}$, $A_{2B}$ and $A_3$. Adenosine $A_{2A}$ receptors are located on blood vessels where they mediate vasodilation (Ueeda, M., et al., *J. Med. Chem.* 34:1334–1339 (1991); Ueeda, M., et al., *J. Med. Chem.* 34:1340–1344 (1991); Niiya, K., et al., *J. Med. Chem.* 35:4557–4561 (1992), Niiya, K., et al., *J. Med. Chem.* 35:4562–4566 (1992); and Glover, D. K., et al., *Circulation* 94:1726–1732 (1996)), on platelets where they mediate an inhibition of aggregation (Cristalli, G., et al., *Arch. Pharmacol.* 349:644–650 (1994); and Varani, K., et al., *Biochem. Pharmacol.* 48:1658–1661 (1994)) and on neutrophils where they mediate inhibition of adherence to endothelial cells and release of toxic oxygen products (Cronstein, B. N., et al., *J. Clin. Invest.* 85:1150–1157 (1990), Cronstein, B. N., et al., *J. Immunol.* 148:2201–2206 (1992); and Sullivan, G. W., et al., *Int. J. Immunopharmac.* 17:793–803 (1995)). A compound that selectively activates only the $A_{2A}$ adenosine receptors is expected to have anti-inflammatory actions in ischemic tissue by virtue of these three properties. Activation of $A_1$ receptors on neutrophils promotes chemotaxis and thereby increases migration of neutrophils to the site of injury. In addition, activation of $A_1$ receptors increases adherence of neutrophils to the endothelium. Adenosine's actions at the $A_1$ receptor are therefore pro-inflammatory (Cronstein, B. N., et al., *J. Clin. Invest.* 85:1150–1157 (1990), and Cronstein, B. N., et al., *J. Immunol.* 148:2201–2206 (1992)). Stimulation of $A_{2A}$-receptors and avoidance of $A_1$-receptor activation are the basis of this invention.

In vitro studies using human neutrophils have shown that $A_{2A}$ selective agonists inhibit the release of oxygen free radicals and proteolytic enzymes from activated neutrophils and inhibit adherence of activated neutrophils to the endothelium (Cronstein, B. N., et al., *J. Immunol.* 148:2201–2206 (1992), Cronstein, B. N., et al., *J. Clin. Invest.* 85:1150–1157 (1990); and Sullivan, G. W., et al., *Int. J. Immunopharmac.* 17:793–803 (1995)). An $A_{2A}$ selective agonist has also been shown to inhibit both the adhesion of activated canine neutrophils to canine cardiac myocytes and to reduce oxidative injury (Bullough, D. A., et al., *J. Immunol.* 155:2579–2586 (1995)). Studies in pigs have shown that there is an increase in platelet deposition and neutrophil adhesion at the site of arterial injury produced by balloon inflation during angioplasty (Merhi, Y., et al., *Circulation* 90:997–1002 (1994); and Provost, P. and Merhi, Y., *J. Pharmacol. Exp. Ther.* 277:17–21 (1996)).

Sollevi, in U.S. Pat. No. 5,449,655, discloses a method for percutaneous transluminal angioplasty comprising the concomitant continuous administration of adenosine to provide the beneficial properties of vasodilation, inhibition of platelet aggregation, and inhibition of presynaptic neural mechanisms regulating release of catecholamines.

Sollevi, in U.S. Pat. No. 5,534,504, discloses a method for coronary thrombolysis comprising the concomitant administration of adenosine with the thrombolytic agent to provide the above properties.

Bru-Magniez, et al., in U.S. Pat. No. 5,459,132, discloses certain $N^6$-substituted adenosine derivatives that are claimed as analgesics, anti-hypertensives and anti-proliferative agents used to treat cancer, psoriasis, atherosclerosis and restenosis phenomena.

Impaired blood flow to organs in mammals commonly results from occlusion of blood vessels as a result of atherosclerosis. Insufficient blood flow causes tissue ischemia and can result in morbidity such as myocardial infarction, stroke, or renal failure. Treatment options include invasive surgical procedures, such as angioplasty, atherectomy, or endarterectomy procedures, as well as the insertion of bypass grafts or stents to restore normal blood flow. A major limitation of the effectiveness of these treatments is that in a large proportion of subjects such cleared blood vessels can again become blocked within months.

Thus, the need continues to exist for methods and compositions that can be employed to reduce or prevent restenosis following an invasive revascularization procedure.

SUMMARY OF THE INVENTION

A first aspect of the present invention concerns a method of reducing or preventing restenosis following a revascularization procedure in a mammal, comprising administering a pharmaceutical composition comprising a pharmaceutically acceptable carrier or diluent and an active agent selected from the group consisting of: (a) a selective adenosine $A_{2A}$ receptor agonist, (b) the combination of a selective adenosine $A_1$ antagonist and either a selective adenosine $A_{2A}$ receptor agonist or a non-selective adenosine agonist, and (c) a selective adenosine $A_1$ antagonist (in order to block the adenosine $A_1$ receptor activation by endogenously-released adenosine, while allowing for adenosine $A_{2A}$ receptor activation by endogenously-released adenosine).

A second aspect of the present invention concerns compositions useful in the reduction and prevention of restenosis following revascularization. These compositions may comprise either: (a) a selective adenosine $A_{2A}$ receptor agonist, (b) the combination of a selective adenosine $A_1$ antagonist and either a selective adenosine $A_{2A}$ receptor agonist or a non-selective adenosine agonist, or (c) a selective adenosine $A_1$ antagonist (in order to block the adenosine $A_1$ receptor activation by endogenously-released adenosine, while allowing for adenosine $A_{2A}$ receptor activation by endogenously-released adenosine).

A third aspect of the present invention provides for the use of one of the following for the manufacture of a medicament for reducing or preventing restenosis following revascularization in mammals: (a) a selective adenosine $A_{2A}$ receptor agonist, (b) the combination of a selective adenosine $A_1$ antagonist and either a selective adenosine $A_{2A}$ receptor agonist or a non-selective adenosine agonist, or (c) a selective adenosine $A_1$ antagonist.

A fourth aspect of the present invention provides for a surgical process, comprising:

(i) administering to a subject a pharmaceutical composition comprising a pharmaceutically acceptable carrier or diluent and an active agent selected from the group consisting of: (a) a selective adenosine $A_{2A}$ receptor agonist, (b) the combination of a selective adenosine $A_1$ antagonist and either a selective adenosine $A_{2A}$ receptor agonist or a non-selective adenosine agonist, and (c) a selective adenosine $A_1$ antagonist (in order to block the adenosine $A_1$ receptor activation by endogenously-released adenosine, while allowing for adenosine $A_{2A}$ receptor activation by endogenously-released adenosine); and (ii) practicing a revascularization procedure on said subject to remove an occlusion or to reroute blood flow through a bypass graft.

DETAILED DESCRIPTION OF THE PREFERRED EMBODIMENTS

It has now been found that selective stimulation of adenosine $A_{2A}$ receptors can reduce or prevent restenosis following revascularization. Adenosine $A_{2A}$ receptors can be selectively stimulated by compositions including either: (a) a selective adenosine $A_{2A}$ receptor agonist, (b) the combination of a selective adenosine $A_1$ antagonist and either a selective adenosine $A_{2A}$ receptor agonist or a non-selective adenosine agonist, or (c) a selective adenosine $A_1$ antagonist in order to block the adenosine $A_1$ receptor activation by endogenously-released adenosine are useful in the prevention and treatment of restenosis following revascularization.

A surgical procedure is provided, comprising:

(i) administering to a subject a pharmaceutical composition comprising a pharmaceutically acceptable carrier or diluent and an active agent selected from the group consisting of: (a) a selective adenosine $A_{2A}$ receptor agonist, (b) the combination of a selective adenosine $A_1$ antagonist and either a selective adenosine $A_{2A}$ receptor agonist or a non-selective adenosine agonist, and (c) a selective adenosine $A_1$ antagonist (in order to block the adenosine $A_1$ receptor activation by endogenously-released adenosine, while allowing for adenosine $A_{2A}$ receptor activation by endogenously-released adenosine); and (ii) practicing a revascularization procedure on said subject to remove an occlusion or to reroute blood flow through a bypass graft.

The procedure of the invention represents an improvement over the prior art in that the degree of restenosis is reduced.

A variety of revascularization procedures can be used, including percutaneous transluminal coronary angioplasty (PTCA), directional coronary atherectomy (DCA) and excimer laser angioplasty. In order to provide improved blood flow in the heart, insertion of coronary artery bypass grafts can be employed. PTCA is an alternative procedure that is also conducted in patients whose coronary blood flow is severely impaired by the presence of atherosclerotic plaques within the coronary blood vessels. In this procedure, a balloon catheter is inserted into coronary blood vessels and inflated at the site of the stenosis in an attempt to disrupt the atherosclerotic plaque and/or distend the disease-free area of the vessel to restore coronary blood flow.

In the present invention, a method of reducing or preventing restenosis following revascularization procedures is provided wherein a mammal, preferably a human, is administered an effective amount of either: (a) a selective adenosine $A_{2A}$ receptor agonist, (b) the combination of a selective adenosine $A_1$ antagonist and either a selective adenosine $A_{2A}$ receptor agonist or anon-selective adenosine agonist, or (c)

a selective adenosine $A_1$ antagonist in order to block the adenosine $A_1$ receptor activation by endogenously-released adenosine. A composition including one of (a), (b) or (c) is administered starting at a selected time prior to the revascularization procedure and is administered in an effective amount such that restenosis is reduced or prevented. Administration is preferably continued following the procedure for a period of up to two days.

Preferably, the compositions and methods of the present invention employ a selective adenosine $A_{2A}$ receptor agonist.

The term "selective stimulation of adenosine $A_{2A}$ receptors" refers to a substantially greater stimulation of adenosine $A_{2A}$ receptors compared to adenosine $A_1$ receptors. Selective stimulation occurs when the ratio of $A_{2A}$: $A_1$ stimulation for a particular agent or combination of agents is greater than the $A_{2A}$: $A_1$ stimulation ratio obtained when adenosine alone is employed as the agent.

The term "effective amount" refers either to: (a) a concentration of an adenosine $A_{2A}$ receptor agonist, (b) a concentration of an adenosine $A_1$ receptor antagonist in combination with a concentration of either a selective adenosine $A_{2A}$ receptor agonist or a non-selective adenosine agonist, or (c) a concentration of a selective adenosine $A_1$ antagonist (to counteract the adenosine $A_1$ receptor activation by endogenously released adenosine) that is sufficient to allow selective adenosine $A_{2A}$ receptor activation by endogenously released adenosine in response to the induced ischemia from the revascularization procedure.

The term "selective adenosine $A_{2A}$ receptor agonist" refers to agonists that stimulate preferentially the adenosine $A_{2A}$ receptor and do not stimulate substantially the adenosine $A_1$ receptor. Compounds may be chosen as selective $A_{2A}$ agonists by testing for cardiovascular activity as described in Niiya, K., et al., *J. Med. Chem.* 35:4557–4561 (1992) and demonstrating an $A_1/A_2$ selectivity ratio therein defined as greater than approximately 100. As will be appreciated by one of ordinary skill in the art, other assays can be employed to screen for adenosine $A_{2A}$ receptor agonism.

Examples of selective adenosine $A_{2A}$ receptor agonists include: 2-(substituted amino)adenosine 5'-carboxamides, described in U.S. Pat. No. 4,968,697; 2-(substituted amino) adenosines, described in U.S. Pat. No. 5,034,381; imidazo-[4,5-b]-pyridine derivatives, described in U.S. Pat. No. 4,977,144; and 2-(substituted alkynyl)adenosines, described in U.S. Pat. No. 5,189,027. Additional examples of selective $A_{2A}$ receptor agonists include 2-hydrazoadenosines, described in U.S. Pat. No. 5,278,150 and 2-aralkoxy and 2-alkoxy adenosines, described in U.S. Pat. No. 5,140,015.

Examples of agonists selective for adenosine $A_{2A}$ receptors include, but are not limited to, 2-cyclohexylmethylenehydrazinoadenosine, 2-(3-cyclohexenyl)methylenehydrazinoadenosine, 2-isopropylmethylenehydrazinoadenosine, N-ethyl-1'-deoxy-1'-[6-amino-2-[(2-thiazolyl)ethynyl]-9 H-purin-9-yl]-β-D-ribofuranuronamide, N-ethyl-1'-deoxy- 1'-[6-amino-2-[hexynyl]-9 H-purin-9-yl]-β-D-ribofuranuronamide, 2-(1 -hexyn-1-yl)adenosine-5'-N-methyluronamide, 5'-chloro-5'-deoxy-2-(1-hexyn-1-yl) adenosine, $N^6$-[2-(3,5-dimethoxyphenyl)-2-(2-methylphenyl)adenosine, 2-(2-phenyl)ethoxyadenosine, 2-[2-(4-methylphenyl)ethoxy]adenosine, 2-[2-(4-fluorophenyl)ethoxy]adenosine, 2-(2-(2-naphthyl)ethoxy) adenosine, 2-[p-(2-carboxyethyl)phenethylamino-5'-N-ethylcarboxarnidoadenosine (CGS-21680), 2-(2-cyclohexyl)ethoxyadenosine, 2-octynyladenosine (YT-146), 2-thiazolylethynyladenosine and 2-phenethylamino-5'-N-ethylcarboxamidoadenosine (CGS-21577).

Preferred selective $A_{2A}$ agonists include 2-cyclohexylmethylenehydrazinoadenosine, 2-(3-cyclohexenyl)methylenehydrazinoadenosine, 2-isopropylmethylenehydrazinoadenosine, 2-(2-phenyl) ethoxyadenosine, 2-(2-(4-methylphenyl)ethoxyadenosine, 2-(2-cyclohexyl)ethoxyadenosine, and 2-(2-(p-carboxyethyl)phenyl)ethylamino-5'-N-ethyl-carboxamidoadenosine.

The term "selective adenosine $A_1$ receptor antagonist" refers to antagonists that bind preferentially to the adenosine $A_1$ receptor and do not bind substantially to adenosine $A_{2A}$ or $A_{2B}$ receptors. Compounds may be chosen as selective $A_1$ antagonists by screening for cardiovascular activity as described in Belardinelli, et al., *J. Pharm. Exp. Ther.* 275:1167–1176 (1995)), and demonstrating that the compound produces a statistically significantly (vs. control) greater blockade of the $A_1$ receptor mediated increase in S-H interval as compared with the blockade of the $A_2$ receptor mediated increase in coronary conductance. As will be appreciated by one of ordinary skill in the art, different assays can be employed to screen for $A_1$ selective antagonism.

Examples of selective adenosine $A_1$ receptor antagonists include: [[2,3,76,9-tetrahydro-1,3-dialkyl-2,6-dioxo-1H-purin-8-yl]alkyl]phenyl heteroalkanoic acids and esters thereof, described in U.S. Pat. No. 5,208,240; 1,3-dialkyl-8-(substituted phenyl)xanthines, described in U.S. Pat. No. 4,783,530; epoxides of 1,3-dialkylxanthines and adenosines, described in U.S. Pat. No. 5,446,046; 8-tricycloalkyl substituted 1,3-dialkylxanthines, described in U.S. Pat. No. 5,395,836; and 1,3-dialicyclicalkyl-8-substituted xanthines. Additional examples of compounds that act as selective $A_1$ receptor antagonists include $N^6$-substituted 9-methyladenines as described in U.S. Pat. No. 5,066,655, published International application WO 96/06845, and U.S. application Ser. No. 08/299,992.

Examples of antagonists selective for adenosine $A_1$ receptors include, but are not limited to, (±)-$N^6$-endonorbornan-2-yl-9-methyladenine (N-0861), (±)-$N^6$-[endo-2'-norbornyl]-8-(isopropylmethylamino)-9-methyladenine, (±)-$N^6$-[endo-2'-(endo-5'-hydroxy)-norbornyl]-8-(isopropylmethylamino)-9-methyladenine, 8-cyclopentyl-1, 3-dipropylxanthine (DPCPX), xanthine amine congener (XAC), 8-(noradamantan-3-yl)-1,3-dipropylxanthine (NAX), 8-(cyclopentan-3-one)-1,3-dipropylxanthine (KFM19), 8-(dicyclopropylmethyl)-1,3-dipropylxanthine (KF-15372), (R)-7,8-dimethyl-2-phenyl-9-(1-phenylethyl)-7-deazaadenine, 1-propyl-3-(4-amino-3-iodophenylethyl)-8-cyclopentylxanthine (BW-A844U), (+)-(R)-[(E)-3-(2-phenylpyrazolo[1,5-a]pyridin-3-yl)acryloyl]-2-piperidine ethanol (FK453), 7-[2-[ethyl(2-hydroxyethyl)amino]ethyl]-3,7-dihydro-1,3-dimethyl-8-(phenylmethyl)-1H-purine-2,6-dione (bamiphylline), 1,3-dipropyl-8-sulfophenylxanthine (DPSPX), 1,3-dipropyl-8-[2-(5,6-exo-epoxy)-(1S,2S)-norborn-2-yl]xanthine (CVT-124), and 7,8-dihydro-8-ethyl-2-(3-noradamantyl)-4-propyl-1H-imidazo[2,1i]purin-5 (4H)-one.

The term "non-selective adenosine agonist" refers to agonists that bind to adenosine $A_1$, $A_{2A}$, and $A_{2B}$ receptors. Compounds may be chosen as non-selective agonists by testing for cardiovascular activity as described in Ueeda, M., et al., *J. Med. Chem.* 34:1334–1339 (1991) and demonstrating an $A_1/A_2$ selectivity ratio therein defined between about 5 and about 100. Examples of non-selective agonists include, but are not limited to, adenosine, 5'-N-ethylcarboxamidoadenosine (NECA), and 2-chloroadenosine.

The present invention provides for the reduction or prevention of restenosis following activation of neutrophils by selectively activating adenosine $A_{2A}$ receptors during revascularization procedures. The present method will not only greatly reduce or prevent ischemic injury due to adherence and release of toxic oxygen products from neutrophils, but will also inhibit the subsequent activation of platelets that leads to the no-reflow phenomenon and restenosis.

The no-reflow phenomenon that occurs in about 5% of patients undergoing PTCA is believed to be due to aggregation of platelets and neutrophils, which causes a blockage of blood flow within the vessels and vasoconstriction from substances released from the platelets. The acute complication rate following PTCA can be reduced by aspirin, which inhibits platelet aggregation. Consequently, aspirin is routinely administered during angioplasty procedures. Aspirin, however, has been shown to have very little effect on the delayed complication rate of restenosis. In addition, aspirin can inhibit the production of vasodilatory prostaglandins and thereby exacerbate vasospasm that can occur following PTCA. In contrast, the present invention is superior to aspirin in reducing acute blood vessel closure following angioplasty procedures by producing a direct inhibition of platelet aggregation (Cristalli, G., et al., *Arch. Pharmacol.* 349:644–650 (1994); and Varani, K., et al., *Biochem. Pharmacol.* 48:1658–1661 (1994)) while having the added benefit of causing vasodilation.

Although deposition of platelets and thrombus formation have been demonstrated to contribute to restenosis following angioplasty, antiplatelet or antithrombotic therapy have generally been demonstrated to have little effect on restenosis after balloon angioplasty (Barry, W. L. and Sarembock, I. J., *Anticoag. Antiplatelet Ther.* 12:517–535 (1994)). This may partly be due to the fact that all of the agents tested to date in humans are relatively weak and non-specific inhibitors of platelet function. Also, restenosis is a multifactorial effect and blocking the action of the platelets alone may not be sufficient to inhibit restenosis. The present invention provides a method to prevent ischemic injury and restenosis as a result of inhibition of both neutrophil activation and platelet activation.

In the present invention, compositions are also provided that are useful in the reduction or prevention of restenosis following revascularization procedures in a mammal, preferably a human. Such compositions comprise either: (a) a selective adenosine $A_{2A}$ receptor agonist, (b) the combination of a selective adenosine $A_1$ antagonist and a nonselective adenosine agonist, or (c) a selective adenosine $A_1$ antagonist in order to block the adenosine $A_1$ receptor activation by endogenously-released adenosine in response to the induced ischemia from the revascularization procedure.

In addition to the pharmacologically active compounds, the pharmaceutical compositions can contain suitable pharmaceutically acceptable carriers comprising excipients and auxiliaries that facilitate processing of the active compounds into preparations that can be used pharmaceutically. Pharmaceutically acceptable carriers include, but are not limited to, saline, water or an aqueous dextrose solution, Molecusol™ or similar sugar solution, combinations of ethanol and aqueous buffer solutions that are commonly used in the art (for example, phosphate buffers), and dilute sodium hydroxide (approx. 0.2 N) solutions. Suitable lipophilic solvents or vehicles include synthetic fatty acid esters, for example, ethyl oleate or triglycerides or polyethylene glycol 400. As will be appreciated, various carrier and/or excipients may be called for depending upon the solubility of the particular agent employed.

The dosage of selective $A_{2A}$ agonist administered will be dependent upon the age, health, and weight of the recipient, kind of concurrent treatment, if any and potency of the particular agonist. Dosages for many known $A_{2A}$ agonists are described in the prior art. Optimized doses can be determined by one or ordinary skill in the art by routine experimentation.

The ratio of an adenosine $A_1$ antagonist and either a selective adenosine $A_2$ agonist or a nonselective agonist will depend on the potencies of the individual agents. However, the combination should be selected such that its $A_1/A_2$ selectivity ratio is greater than approximately 100 as defined in Niiya, K., et al., *J. Med. Chem.* 35:4557–4561(1992). Adjusting the concentrations of each agent based upon their relative potencies to arrive at the required selective stimulation of $A_{2A}$ receptors can be accomplished by the artisan of ordinary skill employing routine experimentation.

It is preferred that compositions of the present invention be administered prior to revascularization procedures, preferably 30 minutes prior to performing revascularization procedure, and then be continuously administered for up to 2 days, preferably for 1 day after the revascularization procedure, preferably by continuous infusion. However, repeated bolus injections can be employed.

It is preferred that these compositions be administered by intravenous bolus injection or infusion directly to the vasculature involved in these revascularization procedures.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

Reduction of Restenosis by Administering an Adenosine $A_{2A}$ Selective Agonist Focal femoral atherosclerosis is induced in rabbits by air desiccation endothelial injury followed by a 2% cholesterol, 6% peanut oil diet for one month. The degree of arterial stenosis is assessed angiographically. At this time, balloon angioplasty is performed using a 2.5 mm balloon, which is inserted into the region of stenosis and inflated with three 60-second, 10-atmosphere inflations 60 seconds apart. This procedure is similar to that used in humans for clearing coronary blood vessels. Rabbits receive an intravenous infusion of 2-cyclohexylmethylenehydrazinoadenosine (0.6 μg/kg/min) or vehicle starting 10 minutes before the angioplasty procedure and continuing for 1 day following angioplasty. Angiograms are performed before and after angioplasty and at 28 days after angioplasty. These angiograms are analyzed quantitatively for decrease of arterial stenosis. Rabbits are sacrificed 28 days following angioplasty and arteries are analyzed histopathologically and morphometrically. The degree of arterial stenosis in the rabbit group treated with the adenosine $A_{2A}$ selective agonist is significantly less than the arterial stenosis in the rabbit group treated with vehicle.

EXAMPLE 2

Reduction of Restenosis by Co-Administration of an Adenosine $A_1$ Antagonist and a Non-Selective Adenosine Agonist Example 1 is followed, with the exception that one rabbit group is treated with an effective amount of a combination of (±)-N⁶-endonorboman-2-yl-9-methyladenine (0.25 mg/kg/min) and 5'-N-ethylcarboxamidoadenosine (6 µg/kg/min) instead of 2-cyclohexylmethylenehydrazinoadenosine. The degree of arterial stenosis in the rabbit group treated with the combination of a selective adenosine $A_1$ antagonist ((±)-N⁶-endonorboman-2-yl-9-methyladenine) and a non-selective adenosine agonist (5'-N-ethylcarboxamidoadenosine) is significantly less than the arterial stenosis in the rabbit group treated with vehicle.

EXAMPLE 3

Reduction of Restenosis by Co-Administration of an Adenosine $A_1$ Antagonist and an Adenosine $A_{2A}$ Selective Agonist Example 1 is followed, with the exception that one rabbit group is treated with an effective amount of a combination of (±)-N⁶-endonorbornan-2-yl-9-methyladenine (0.25 mg/kg/min) and 2-cyclohexylmethylenehydrazinoadenosine (0.6 µg/kg/min) instead of 2-cyclohexylmethylenehydrazinoadenosine alone. The degree of arterial stenosis in the rabbit group treated with this combination is significantly less than the arterial stenosis in the rabbit group treated with vehicle.

EXAMPLE 4

Reduction of Restenosis by Administering a Selective Adenosine $A_1$ Antagonist

Example 1 is followed, with the exception that the non-vehicle rabbit group is not treated with 2-cyclohexylmethylenehydrazinoadenosine, but with an effective amount of (±)-N⁶-endonorbonan-2-yl-9-methyladenine (0.25 µg/kg/min) in order to block the adenosine $A_1$ receptor activation by endogenously released adenosine in response to the induced ischemia from the revascularization procedure. The degree of arterial stenosis in the rabbit group treated with the selective adenosine $A_1$ antagonist ((±)-N⁶-endonorbonan-2-yl-9-methyladenine) is significantly less than the arterial stenosis in the rabbit group treated with vehicle.

EXAMPLE 5

In Vivo Inhibition of Neutrophil and Platelet Activation by Administering an Adenosine $A_{2A}$ Selective Agonist Humans are subjected to balloon angioplasty, and receive either an intravenous infusion of 2-cyclohexylmethylenehydrazinoadenosine (0.6 µg/kg/min) or vehicle starting 10 minutes before the angioplasty procedure and continuing for 1 day following angioplasty. In vivo activation of neutrophils and platelets are measured by taking a blood sample from the coronary sinus and measuring the expression of surface adhesion molecules on platelets and neutrophils by flow cytometry. The group receiving 2-cyclohexylmethylenehydrazinoadenosine demonstrates significantly fewer platelets and neutrophils that express surface adhesion molecules than the group receiving vehicle.

EXAMPLE 6

Reduction of Restenosis by Administering an Adenosine A2 A Selective Agonist

Humans afflicted with impaired blood flow due to stenotic arteries are subjected to balloon angioplasty, and receive either an intravenous infusion of 2-cyclohexylmethylenehydrazinoadenosine (0.6 µg/kg/min) or vehicle starting 10 minutes before the angioplasty procedure and continuing for 1 day following angioplasty. Six months following the balloon angioplasty procedure, angiography is performed on these subjects to examine the blood vessel subjected to the angioplasty. The incidence of restenosis is significantly less in the group receiving 2-cyclohexylmethylenehydrazinoadenosine than the group receiving vehicle.

Having now fully described this invention, it will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A method of reducing restenosis that occurs following a revascularization procedure, comprising:

administering to a mammal in need of such treatment a pharmaceutical composition comprising a pharmaceutically acceptable carrier or diluent and an active agent selected from the group consisting of:

(a) a selective adenosine $A_{2A}$ receptor agonist, (b) the combination of a selective adenosine $A_1$ antagonist and either a selective adenosine $A_{2A}$ receptor agonist or a non-selective adenosine agonist, and (c) a selective adenosine $A_1$ antagonist in order to block the adenosine $A_1$ receptor activation by endogenously released adenosine;

wherein said active agent is administered starting at a selected time prior to a revascularization procedure and is administered in an effective amount such that restenosis is reduced.

2. The method of claim 1, wherein said pharmaceutical composition is administered beginning 30 minutes prior to said revascularization procedure.

3. The method of claim 2, wherein said pharmaceutical composition is administered continuously for up to two days after said revascularization procedure.

4. The method of claim 1, wherein said pharmaceutical composition is administered by intravenous bolus injection or by infusion directly to the vasculature being treated by said revascularization procedure.

5. The method of claim 1, wherein the revascularization procedure is performed on one or more of coronary arteries, carotid arteries, renal arteries, or leg arteries.

6. The method of claim 1, wherein the revascularization procedure is one of balloon angioplasty, insertion of a bypass graft, insertion of a stent, percutaneous transluminal coronary angioplasty, or directional coronary atherectomy.

7. The method of claim 1, wherein the revascularization procedure involves excimer laser angioplasty.

8. The method of claim 1, wherein the mammal is a human.

9. The method of claim 1, wherein the agent is a selective $A_{2A}$ receptor agonist.

10. The method of claim 9, wherein the selective $A_{2A}$ receptor agonist is selected from the group consisting of:

2-cyclohexylmethylenehydrazinoadenosine, 2-(3-cyclohexenyl)methylenehydrazinoadenosine, 2-isopropylmethylenehydrazinoadenosine, N-ethyl-1'-deoxy-1'-(6-amino-2-((2-thiazolyl)ethynyl)-9H-purin-9-yl)-β-D-ribofuranuronamide, N-ethyl-1'-deoxy-1'-(6-amino-2-(hexynyl)-9H-purin-9-yl)-β-D-ribofuranuronamide, 2-(1-hexyn-1-yl)adenosine-5'-N-methyluronamide, 5'-chloro-5'-deoxy-2-(1-hexyn-1-yl)adenosine, $N^6$-(2-(3,5-dimethoxyphenyl)-2-(2-methylphenyl) adenosine, 2-(2-phenyl)ethoxyadenosine, 2-(2-(4-methylphenyl)ethoxy)adenosine, 2-(2-(4-fluorophenyl)ethoxy)adenosine, 2-(2-(2-naphthyl)ethoxy)adenosine, 2-(p-(2-carboxyethyl)phenyl)ethylamino-5'-N-ethyl-carboxamidoadenosine, 2-(2-cyclohexyl)ethoxyadenosine, 2-octynyladenosine, 2-thiazolylethynyladenosine, and 2-phenethylamino-5'-N-ethylcarboxamidoadenosine.

11. The method of claim 10, wherein said selective $A_{2A}$ agonist is 2-cyclohexylmethylenehydrazinoadenosine, 2-(3-cyclohexenyl)methylenehydrazinoadenosine, 2-isopropylmethylenehydrazinoadenosine, 2-(2-phenyl) ethoxyadenosine, 2-(2-(4-methylphenyl)ethoxyadenosine, 2-(2-cyclohexyl)ethoxyadenosine, or 2-(2-(p-carboxyethyl) phenyl)ethylamino-5'-N-ethyl-carboxamidoadenosine.

12. The method of claim 1, wherein said agent is a selective $A_1$ receptor antagonist.

13. The method of claim 12, wherein said agent is a selective $A_1$ receptor antagonist selected from the group consisting of:

(±)-endonorbornan-2-yl-9-methyladenine, (±)-$N^6$-[endo-2'-norbornyl]-8-(isopropylmethylamino)-9-methyladenine, (±)-$N^6$-[endo-2'-(endo-5'-hydroxy)-norbornyl]-8-(isopropylmethylamino)-9-methyladenine, 8-cyclopentyl-1,3-dipropylxanthine, xanthine amine congener, 8-(noradamantan-3-yl)-1,3-dipropylxanthine, 8-(cyclopentan-3-one)-1,3-dipropylxanthine, 8-(dicyclopropylmethyl)-1,3,dipropylxanthine, (R)-7,8-dimethyl-2-phenyl-9-(1-phenylethyl)-7-deazaadenine, 1-propyl-3-(4-amino-3-iodophenylethyl)-8-cyclopentylxanthine, (+)-(R)-[(E)-3-(2-phenylpyrazolo[1,5-a]pyridin-3-yl) acryloyl]-2-piperidine ethanol, 7-[2-[ethyl(2-hydroxyethyl)amino]ethyl]-3,7-dihydro-1,3-dimethyl-8-(phenylmethyl)-1H-purine-2,6-dione, 1,3-dipropyl-8-sulfophenylxanthine, 1,3-dipropyl-8-[2-(5,6-exo-epoxy)-(1S,2S)-norborn-2-yl] xanthine, and 7,8-dihydro-8-ethyl-2-(3-noradamantyl)-4-propyl-1H-imidazo[2,1-i]purin-5(4H)-one.

14. The method of claim 12, wherein said agent further comprises a non-selective adenosine agonist selected from the group consisting of adenosine, 5'-N-ethylcarboxamidoadenosine and 2-chloroadenosine.

15. The method of claim 9, wherein the selective $A_{2A}$ receptor agonist is a 2-hydrazoadenosine compound.

16. The method of claim 15, wherein the 2-hydrazoadenosine compound is selected from the group consisting of 2-cyclohexylmethylenehydrazinoadenosine, 2-(3-cyclohexenyl)methylenehydrazinoadenosine, and 2-isopropylmethylenehydrazinoadenosine.

* * * * *